United States Patent
Greco

[11] Patent Number: 5,842,467
[45] Date of Patent: Dec. 1, 1998

[54] METERED DOSE INHALER AND AMBULATORY MANUAL BREATHING UNIT COMBINATION

[76] Inventor: Michael Greco, 43 Main St., Garnerville, N.Y. 10923

[21] Appl. No.: 665,942
[22] Filed: Jun. 19, 1996
[51] Int. Cl.⁶ .................... A61M 11/00; A61M 16/00; A62B 9/02
[52] U.S. Cl. ............... 128/200.23; 128/205.13; 128/203.28
[58] Field of Search .................... 128/203.28, 203.18, 128/200.23, 203.12, 205.13–205.17

[56] References Cited

U.S. PATENT DOCUMENTS

| | | | |
|---|---|---|---|
| 3,490,452 | 1/1970 | Greenfield | 128/200.23 |
| 4,119,097 | 10/1978 | Spector | 128/203.28 |
| 4,320,754 | 3/1982 | Watson et al. | 128/205.17 |
| 4,452,241 | 6/1984 | Sarnoff . | |
| 4,484,577 | 11/1984 | Sackner et al. | 128/203.28 |
| 4,790,305 | 12/1988 | Zoltan et al. | 128/203.28 |
| 4,938,210 | 7/1990 | Shene . | |
| 5,020,530 | 6/1991 | Miller | 128/203.28 |
| 5,178,138 | 1/1993 | Walstrom . | |
| 5,297,543 | 3/1994 | Larson . | |
| 5,357,946 | 10/1994 | Kee . | |
| 5,359,998 | 11/1994 | Lloyd | 128/203.12 |
| 5,520,173 | 5/1996 | Kuhn | 128/205.14 |
| 5,613,489 | 3/1997 | Miller et al. | 128/203.18 |
| 5,701,886 | 12/1997 | Ryatt | 128/203.12 |

OTHER PUBLICATIONS

"*Manual of Respiratory Care Procedures*", Diane Blodgett, 2nd ed., © 1987; G.B. Lippincott Co., ISBN 0–397507143. Lippincott Co., ISBN O–397507143

*Primary Examiner*—Kimberly L. Asher
*Attorney, Agent, or Firm*—Stanley J. Yavner

[57] ABSTRACT

The use of a large ambulatory manual breathing unit in combination with a metered dose medication inhaler for delivering medication to a patient, who is either breathing spontaneously or non-spontaneously. The large bag or reservoir of the breathing unit is used to insure minimization of size and homogeneous disbursement of the particles of medication. For non-spontaneous patient breathing, the reservoir's contents are disbursed into the patient by manually or mechanically squeezing the bag, after which the bag returns to its original shape and volume. At one or the other end of the bag, a typical metered dose inhalator is mounted in a manner to disburse the medication into the bag, and directly in line therewith, through an adaptor. The metered dose inhaler collar, into which the inhaler fits, when the inhaler is not in use, is capped.

4 Claims, 2 Drawing Sheets

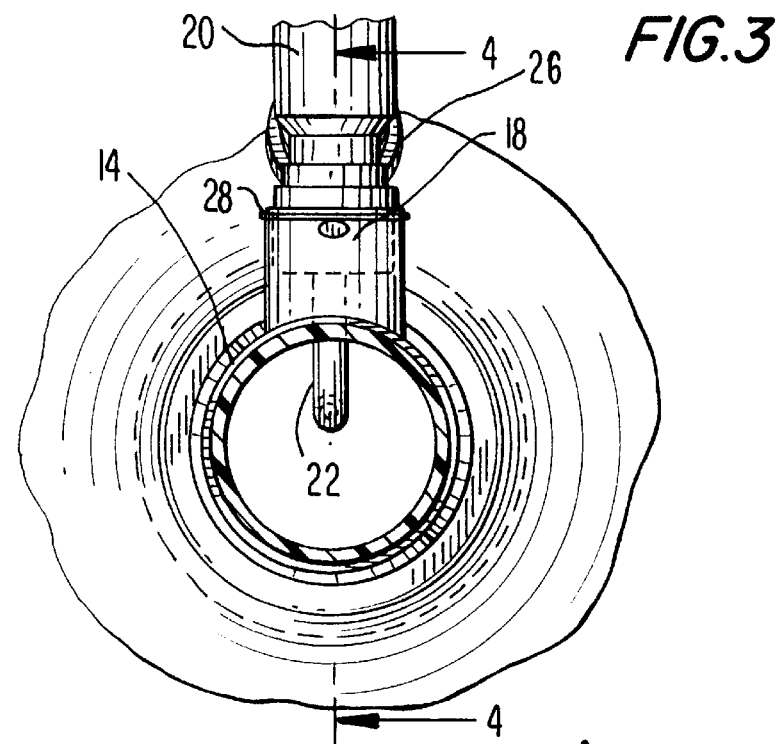
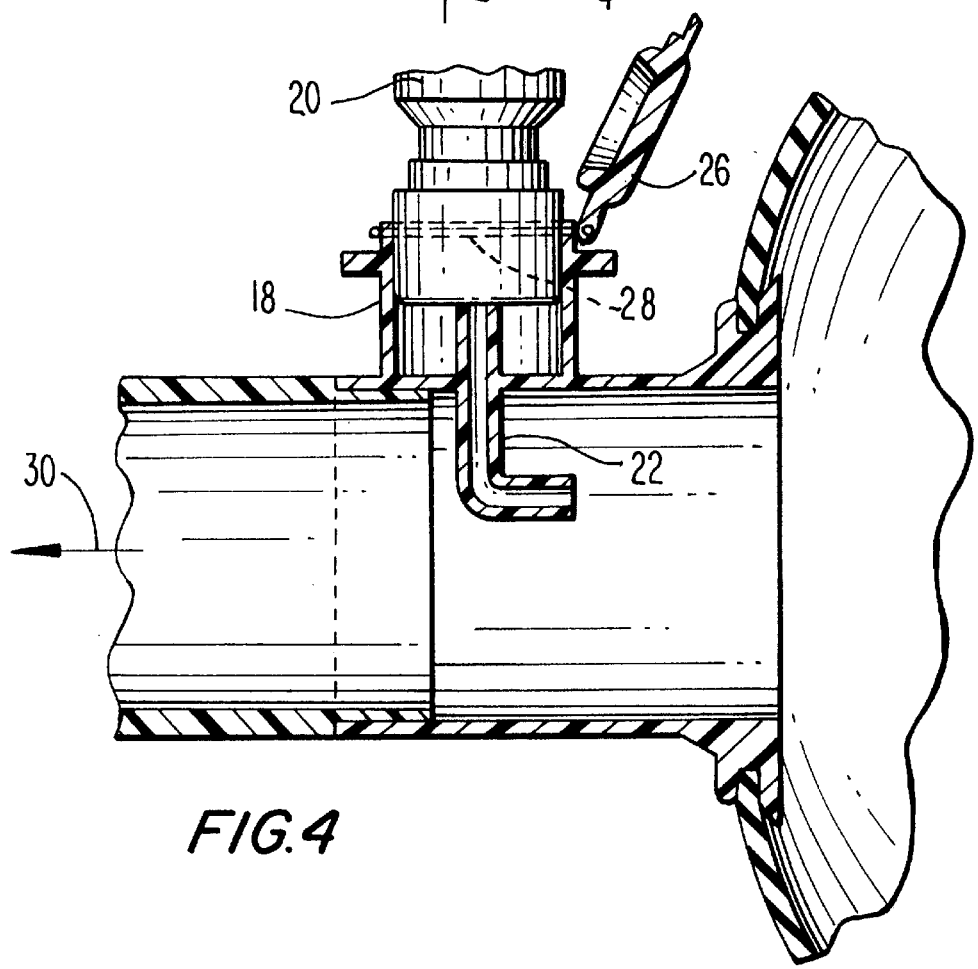

METERED DOSE INHALER AND AMBULATORY MANUAL BREATHING UNIT COMBINATION

FIELD OF THIS INVENTION

This invention relates primarily to metered dose inhalers and ambulatory manual breathing devices, and more particularly to the combination thereof for purpose of functioning as a resuscitation device, as a manual or mechanical breathing device, and without alteration of the basic structures as a unit for dispensing medication into a patient while resuscitation or spontaneous or non-spontaneous breathing is taking place.

BACKGROUND OF THE INVENTION

Oral delivery of drugs using an aerosol canister has been known for many years, but for various reasons, either the patients have failed to properly use these aerosol devices, or otherwise optimum use has not been made. Nevertheless, with respect to a non-spontaneously breathing patient, or with respect to a non-breathing patient, it is sometimes critical to induce breathing, and at the same time apply medication using such aerosol device.

Likewise, for many years, the use of ambulatory manual breathing units has been common, but many times it is necessary to disengage such units from the patient in order to apply medication directly into the patient's mouth.

Many attempts have been made at a combination of the manual breathing unit and the metered dose inhaler, but for various reasons, the designs have not been accepted and used. For instance, the structure shown by Sarnoff, et al, in U.S. Pat. No. 4,452,241 is complex and does not present a sufficient reservoir in which the medication can be homogeneously disbursed and particulated for purposes indicated herein. Likewise, Sackner, et al, U.S. Pat. No. 4,484,577 combines the ambulatory manual breathing unit and the metered dose inhaler, but in a manner which uses a collapsible manual breathing unit bag, which is without rigidity sufficient for use also as an ambulatory manual breathing unit, i.e., with an emergency person manually squeezing the reservoir contents into the patient using positive pressure, the bag returning to its original shape and volume after each squeeze.

Even when a structure has been presented using positive pressure for disbursing the medication into the patient, the collapsibility feature of the ambulatory manual breathing unit bag has not been present. For instance, the patent to Larson, U.S. Pat. No. 5,297,543, is less than satisfactory in this respect, not having a collapsible bag.

Also, with respect to the Kee patent, U.S. Pat. No. 5,357,946, the structure of this patent does not present a reservoir for medication, and the structure is not intended for use with a manual breathing unit bag. Likewise, Walstrom, U.S. Pat. No. 5,178,138, does not present an adapter, defining a groove for coupling with the ambulatory manual breathing unit bag of the present invention; the adapter of Walstrom being distil to the positive pressure created by the spacer in Walstrom and the manual breathing unit bag of the present invention, thereby creating dead air space to the structure. The same comments apply as well to the Shene patent, U.S. Pat. No. 4,938,210.

SUMMARY AND OBJECTS OF THE INVENTION

Accordingly, a primary object of the present invention is to provide a combination ambulatory manual breathing unit, with a resilient, collapsible bag and a metered dose inhaler for simultaneously assisting breathing of a patient while the patient inhales medication.

A further and more particular object is to provide a combination, as described, and with a sufficiently large reservoir for homogeneously disbursing medication in a particulate form of sufficiently small size.

These and other objects of the present invention are provided in a combination structure having an ambulatory manual breathing unit with a stiffly resilient reservoir bag to which is connected a metered dose inhaler, inserted to a collar connected to either end of the reservoir bag of the breathing unit. The metered dose inhaler collar also includes a conveniently removable cap for closing the connecting collar, when the inhaler device is not attached. An adaptor bridges the space between the collar and the reservoir bag and the adaptor defines at one end of the adaptor, a groove for connecting the breathing unit bag or reservoir.

BRIEF DESCRIPTION OF THE DRAWINGS

Other objects, features and advantages of the present invention will become apparent by reference to the following detailed description of the preferred, but nonetheless illustrative, embodiment of the present invention, with reference to the accompanying drawings, wherein:

FIG. 3 is a sectional view taken along the line 3—3 of FIG. 1 and showing particularly the inhaler device, collar, adaptor, ambulatory manual breathing unit reservoir connection and combination according to the present invention; and FIG. 4 is a sectional view taken along the line 4—4 of FIG. 3, with a front view of the combination.

DETAILED DESCRIPTION OF THE PREFERRED EMBODIMENT

Figure 1:
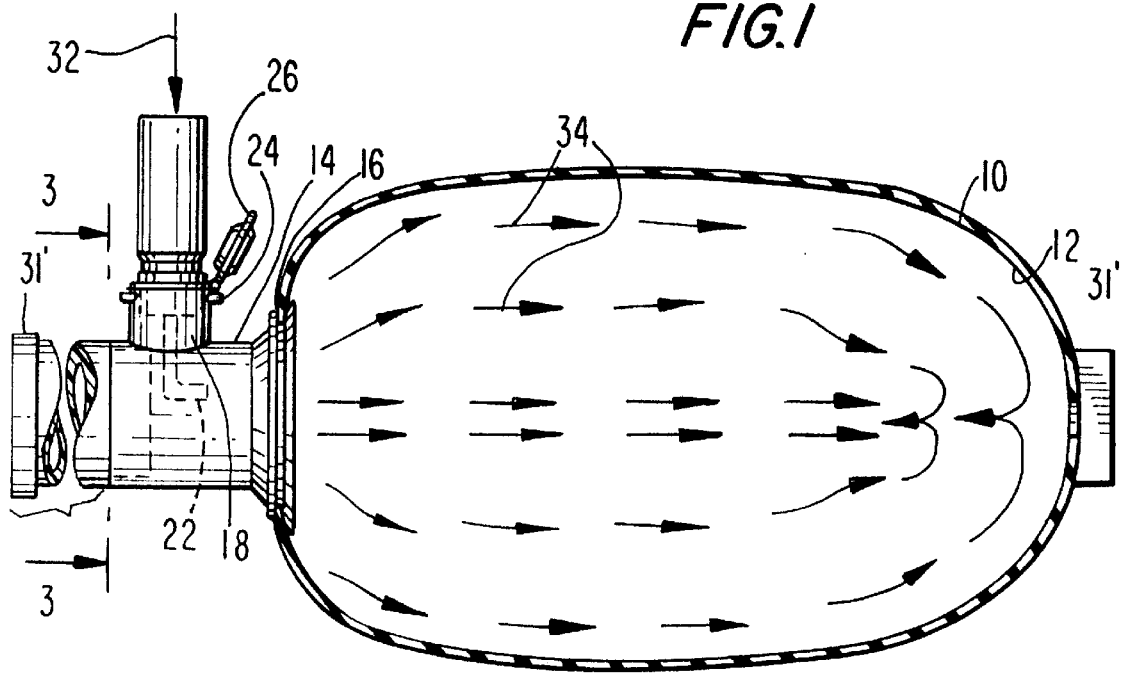
FIG. 1 is a partial front view showing the present invention, with the combination of metered dose inhaler, the collar, and the adaptor bag of the ambulatory manual breathing unit, during medication insertion and/or exhaling by the patient.

Referring to the drawings, the ambulatory manual breathing unit (hereinafter AMBU) is provided to include reservoir bag 10, which defines a large reservoir 12 therein. Also provided by the present invention structure is an adaptor 14 which defines groove 16, into which wall 10 of AMBU bag mates in an air-tight seal.

Collar 18 mates with the metered dose inhaler 20 (hereinafter MDI), and particularly its downspout 22 provides aerosol medication in adaptor 14 in a direction toward AMBU bag 10. More particularly, collar 18 defines therewithin a holding chamber, and extending from the outside of collar 18 are a pair of handles 24 for purposes of the leverage necessary for activating the MDI. As shown in FIG. 3, which provides a more detailed showing of the collar, MDI and adapter, the handle cross-sectional shape is actually oval for ergonomic reasons. As shown in FIG. 4, a cap 26 is attached by loop 28 to collar 18 in order to provide a cover for the collar when the MDI is not in its inserted position.

Referring to FIG. 4, directional arrows 30 indicate the connection of the entire combination structure to either a face mask (not shown), an endotracheal tube for intubation (not shown) or a tracheotomy tube (not shown).

Figure 2:
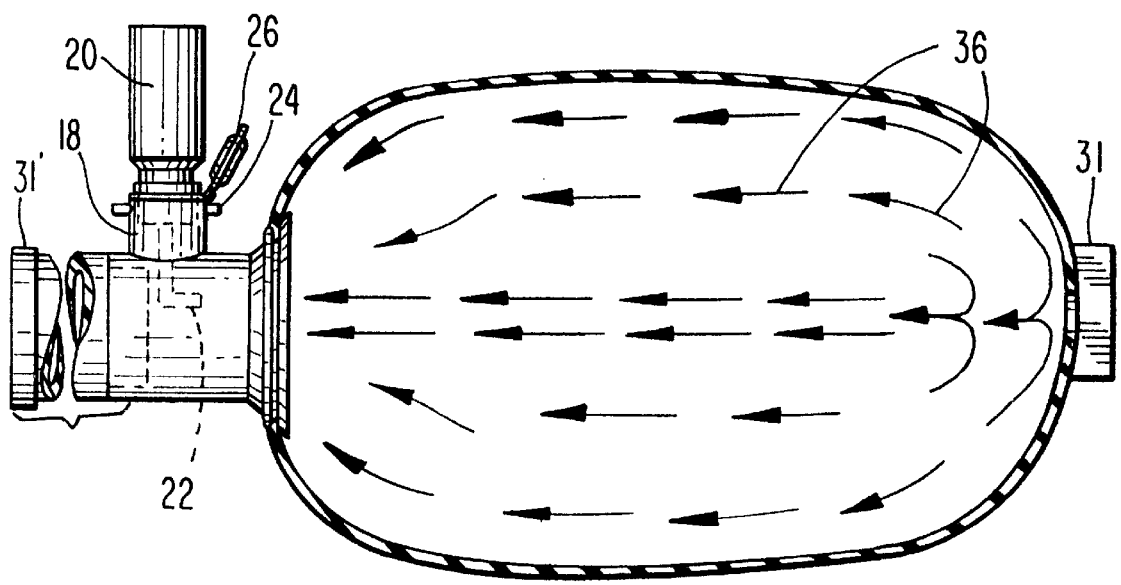
FIG. 2 is a view similar to that of FIG. 1, but showing the direction of flow in the reservoir or bag during inhalation by the patient, and after mediation has been disbursed in the bag.

Of course, with the same effective results, the MDI unit, its collar and the adaptor, alternatively, are attached to the other end of the AMBU bag. Valves 31 and 31' assist in the operation of the present invention. For instance, valves 31 and 31' are one-way valves. More specifically, an exhale port is provided to the left of one-way valve 31', in the orientation of FIG. 2, which closes when valve 31' is opened.

In order to provide a more detailed understanding of the structure of the present invention, a series of use and operation steps is now provided. Specifically, FIG. 1 shows the medication input and/or exhaling steps, whereby medication is provided by pushing in the direction of arrow 32, thereby providing medication in the direction of arrows 34 from the MDI, through downspout 22 within collar 18, and through adaptor 14 into the AMBU bag, where the medication is caused to break into smaller particles and disbursed homogeneously. The insertion of medication into the AMBU bag is, by use as intended, of the MDI 20, thereby to provide flowing of medication in the direction depicted by arrows 34.

The inhaling step begins before absorption orally of the medication by the patient and whereby medication particles 36 are inhaled in direction 30 (FIG. 4) through the AMBU bag by the patient, the medication having been previously provided to the AMBU bag.

As may be seen with all of the foregoing, an AMBU bag accessory to assist breathing and the application of medication is provided in a combination structure as described. The limits of the present invention are not imposed by the foregoing description; and instead are provided only by the following claims:

What is claimed is:

1. A combination structure for use with an ambulatory manual breathing unit on a patient comprising a stiffly resilient reservoir bag having a general shape which defines a pair of ends, a metered dose inhaler unit having a depending downspout for dispensing medication, a collar for supporting said metered dose inhaler unit and an adaptor, into which said depending downspout is inserted, and which defines a groove for connecting said adaptor to said bag, at one end thereof, a one-way valve proximate the end of said reservoir bag, which is distal to the end at which said adaptor is connected to said bag, and a one-way valve proximate said adaptor, for only enabling inhalation by said patient of the contents of said reservoir bag, said valves and the arrangement of said adaptor providing means for dispensing said medication into said reservoir bag, breaking said medication into smaller particles and dispersing said medication homogeneously from said reservoir bag, and then through said adaptor to a spontaneously or non-spontaneously breathing patient using positive pressure.

2. The invention according to claim 1, wherein said collar defines a pair of outwardly projecting handles for use in dispensing said medication from said metered dose inhaler.

3. The invention according to claim 1, wherein said collar includes a removable cap for adapting said combination to a resuscitation device by removing said metered dose inhaler and closing said collar with said cap.

4. The invention according to claim 1, wherein at least one end of said bag defines a lip for mating with said groove.

* * * * *